(12) United States Patent
Brayanov et al.

(10) Patent No.: US 9,595,123 B2
(45) Date of Patent: Mar. 14, 2017

(54) METHODS AND DEVICES FOR DISPLAYING TREND AND VARIABILITY IN A PHYSIOLOGICAL DATASET

(71) Applicant: Respiratory Motion, Inc., Waltham, MA (US)

(72) Inventors: Jordan Brayanov, Medford, MA (US); Malcolm Bock, Medfield, MA (US); Michael Lalli, Somerville, MA (US); Jenny Freeman, Weston, MA (US); Colin M. MacNabb, Allston, MA (US)

(73) Assignee: Respiratory Motion, Inc., Waltham, MA (US)

( * ) Notice: Subject to any disclaimer, the term of this patent is extended or adjusted under 35 U.S.C. 154(b) by 0 days.

(21) Appl. No.: 14/640,648

(22) Filed: Mar. 6, 2015

(65) Prior Publication Data

US 2015/0254880 A1    Sep. 10, 2015

Related U.S. Application Data

(60) Provisional application No. 61/948,964, filed on Mar. 6, 2014.

(51) Int. Cl.
*G06T 11/20* (2006.01)
*G06F 19/00* (2011.01)

(52) U.S. Cl.
CPC .......... *G06T 11/206* (2013.01); *G06F 19/322* (2013.01); *G06F 19/3406* (2013.01)

(58) Field of Classification Search
CPC .................................................... G06T 11/206
USPC ......................................................... 345/440
See application file for complete search history.

(56) References Cited

U.S. PATENT DOCUMENTS

| 3,433,217 A | 3/1969 | Rieke |
| 3,690,143 A | 9/1972 | Day |
| 3,742,936 A | 7/1973 | Blanie |
| 4,036,217 A | 7/1977 | Ito |
| 5,058,583 A | 10/1991 | Geddes et al. |
| 5,469,859 A | 11/1995 | Tsoglin et al. |
| 5,735,284 A | 4/1998 | Tsoglin et al. |

(Continued)

FOREIGN PATENT DOCUMENTS

| CN | 1034665 | 8/1989 |
| EP | 1302217 | 4/2003 |

(Continued)

OTHER PUBLICATIONS

Pajic, et al, Model-driven safety analysis of closed-loop medical systems, IEEE Trans Industr Inform. vol. 10, pp. 1-35, p. 4, para. 1-2, Oct. 28, 2013.

(Continued)

*Primary Examiner* — Javid A Amini
(74) *Attorney, Agent, or Firm* — Remenick PLLC (57) ABSTRACT

Embodiments of the invention are directed to methods and devices for displaying trends and variability in a physiological dataset. The method comprises obtaining the physiological dataset, applying a smoothing algorithm to the physiological dataset to obtain a trend of the physiological dataset, applying a variability algorithm to the physiological dataset to obtain the variability of the physiological dataset, outputting a graph of the trend of the physiological dataset, and outputting a graph of the variability of the physiological dataset.

22 Claims, 6 Drawing Sheets

(56) References Cited

U.S. PATENT DOCUMENTS

| | | | |
|---|---|---|---|
| 5,951,611 A * | 9/1999 | La Pierre | G05B 23/0232 701/32.1 |
| 5,953,441 A | 9/1999 | Setlak | |
| 6,168,568 B1 | 1/2001 | Gavriely | |
| 6,173,198 B1 | 1/2001 | Schulze | |
| 6,286,806 B1 | 9/2001 | Cocoran | |
| 6,366,803 B1 | 4/2002 | Fee | |
| 6,402,697 B1 | 6/2002 | Calkins et al. | |
| 6,408,259 B1 * | 6/2002 | Goebel | B64D 43/00 701/100 |
| 6,809,462 B2 | 10/2004 | Pelrine et al. | |
| 6,976,963 B2 * | 12/2005 | Clift | A61B 5/0205 600/483 |
| 7,069,263 B1 * | 6/2006 | Yee | G06F 17/30551 707/602 |
| 7,196,317 B1 | 3/2007 | Meissner et al. | |
| 7,361,146 B1 * | 4/2008 | Bharmi | A61B 5/02405 600/481 |
| 7,530,956 B2 | 5/2009 | Lewicke et al. | |
| 7,653,512 B2 * | 1/2010 | Cheung | G05B 23/0283 702/1 |
| 8,096,962 B2 | 1/2012 | Palazzolo | |
| 8,306,611 B2 | 11/2012 | Granov et al. | |
| 8,782,504 B2 * | 7/2014 | Narayanan | G06F 11/1004 714/799 |
| 2002/0032383 A1 * | 3/2002 | Weil | A61B 5/0205 600/484 |
| 2004/0071337 A1 * | 4/2004 | Jeung | A61B 5/08 382/151 |
| 2004/0123667 A1 | 7/2004 | McGrath | |
| 2005/0033198 A1 * | 2/2005 | Kehyayan | A61B 7/003 600/586 |
| 2005/0090753 A1 | 4/2005 | Goor et al. | |
| 2005/0107719 A1 * | 5/2005 | Arad (Abbound) | A61B 5/0536 600/547 |
| 2005/0113702 A1 | 5/2005 | Salla et al. | |
| 2005/0234362 A1 * | 10/2005 | Kaiser | A61B 5/044 600/515 |
| 2006/0058600 A1 | 3/2006 | Eichler | |
| 2006/0070623 A1 | 4/2006 | Wilkinson | |
| 2006/0241506 A1 * | 10/2006 | Melker | A61B 5/08 600/529 |
| 2006/0241513 A1 * | 10/2006 | Hatlestad | A61B 5/0809 600/547 |
| 2007/0010764 A1 | 1/2007 | Palazzolo et al. | |
| 2007/0276300 A1 | 11/2007 | Olson et al. | |
| 2008/0312565 A1 | 12/2008 | Celik-Butler et al. | |
| 2009/0062672 A1 * | 3/2009 | Sly | A61B 5/08 600/529 |
| 2009/0149748 A1 | 6/2009 | Lenhardt et al. | |
| 2009/0227849 A1 | 9/2009 | Goor et al. | |
| 2009/0264789 A1 * | 10/2009 | Molnar | A61N 1/36135 600/544 |
| 2009/0264792 A1 | 10/2009 | Mazar | |
| 2009/0326353 A1 | 12/2009 | Watson | |
| 2010/0049071 A1 | 2/2010 | Goor et al. | |
| 2010/0152600 A1 * | 6/2010 | Droitcour | A61B 5/05 600/534 |
| 2010/0228166 A1 | 9/2010 | Centen | |
| 2010/0241181 A1 | 9/2010 | Savage et al. | |
| 2010/0268103 A1 * | 10/2010 | McNamara | G06F 19/3487 600/518 |
| 2011/0077497 A1 | 3/2011 | Oster | |
| 2011/0245712 A1 | 10/2011 | Patterson et al. | |
| 2011/0306850 A1 * | 12/2011 | Hatlestad | A61B 5/0031 600/301 |
| 2012/0041279 A1 * | 2/2012 | Freeman | A61B 5/0205 600/301 |
| 2012/0165883 A1 * | 6/2012 | Kalgren | A61B 5/0006 607/3 |
| 2013/0187941 A1 | 7/2013 | Noon | |
| 2013/0296823 A1 | 11/2013 | Melker et al. | |
| 2014/0073895 A1 | 3/2014 | Brayanov | |
| 2014/0114582 A1 * | 4/2014 | Mittelman | G06F 19/18 702/19 |
| 2014/0304390 A1 * | 10/2014 | Bates | H04L 12/6418 709/224 |

FOREIGN PATENT DOCUMENTS

| | | |
|---|---|---|
| EP | 2008581 | 12/2008 |
| EP | 2018825 | 1/2009 |
| JP | 2000-70370 | 3/2000 |
| JP | 2007-203041 | 8/2007 |
| JP | 2009-240752 | 10/2009 |
| WO | WO00/33733 | 6/2000 |
| WO | WO2007/064682 | 6/2007 |
| WO | WO2007/147505 | 12/2007 |
| WO | WO2008/130549 | 10/2008 |
| WO | WO2009/035965 | 3/2009 |
| WO | WO2009/036312 | 3/2009 |
| WO | WO2010/059049 | 5/2010 |

OTHER PUBLICATIONS

PCT Search Report for PCT/US15/59032, dated Feb. 4, 2016.
EP Office Action for PCT/US2010/047604, dated Mar. 5, 2015.
EP Office Action for PCT/US2011/47812, dated Mar. 11, 2015.
Zulkarneev R Kh. Et al., A Hardware-Software System for Volumetric Calibration of Impedance Pneumograms, Biomedical Engineering, vol. 35, No. 1, 2001, pp. 48-51.
Japenese Office Action for PCT/US2011/047812, dated Mar. 2, 2015.
EPO Search Report for PCT/US2011/047812, dated Feb. 19, 2014.
U.S. Appl. No. 12/677,216, Freeman.
U.S. Appl. No. 13/210,360, Freeman.
U.S. Appl. No. 14/021,939, Freeman.
PCT Search Report for PCT/US2013/058797, dated Feb. 25, 2014.
EP Search Report for PCT/US2011/047812, dated Feb. 19, 2014.
PCT Search Report for PCT/US2012/47604, dated Oct. 12, 2012.
PCT Patentability Report for PCT/US2012/47604, dated Oct. 12, 2012.
PCT Search Report for PCT/US2008/76224, dated Nov. 10, 2008.
PCT Patentability Report for PCT/US2008/76224, dated Nov. 10, 2008.
PCT Search Report for PCT/US2011/47812, dated Jan. 10, 2012.
PCT Patentability Report for PCT/US2011/47812, dated Jan. 10, 2012.
U.S. Appl. No. 12/667,216, filed Dec. 23, 2010, Freeman.
U.S. Appl. No. 13/210,360, filed Feb. 16, 2012, Freeman.
PCT Patentability Report for PCT/US2008/76224, dated Mar. 16, 2010.
PCT Search and Patentability Report for PCT/US2015/19196, dated Jun. 24, 2015.
U.S. Appl. No. 13/554,346, filed Jan. 24, 2013, Freeman.
Bioimpedance Analysis: A Guide to Simple Design and Implementation, by Aroom et al., Journal of Surgical Research, Dec. 17, 2007.

* cited by examiner

METHODS AND DEVICES FOR DISPLAYING TREND AND VARIABILITY IN A PHYSIOLOGICAL DATASET

REFERENCE TO RELATED APPLICATIONS

The present application claims priority to Provisional U.S. Application No. 61/948,964, filed Mar. 6, 2014, entitled "METHODS AND DEVICES FOR DISPLAYING TREND AND VARIABILITY IN A PHYSIOLOGICAL DATASET," and is incorporated herein in its entirety.

BACKGROUND

1. Field of the Invention

The invention is directed to devices and methods for displaying a physiological dataset in graphical form. Specifically, the invention is directed toward devices and methods for displaying trend and variability of a physiological dataset in graphical form.

2. Background of the Invention

Medical professionals use charts of physiological data on a regular basis to come to decisions critical to patient care. Patient information charts have historically been written or printed on paper, however with the advent of electronic displays, charts of patient's data are increasingly found in electronic forms. Everything from patient health information to real-time physiological data is transitioning from paper to electronic form. The transition to electronic form, linked to computers or other programmable equipment, enables new and improved visualizations to be applied to patient data, especially physiological data.

Physiological data is typically acquired from the patient by means of a variety of sensors. Data can be acquired over the course of a patient's life at regularly scheduled exams, or over a series of hours, minutes, or in real-time in the case of continuous monitoring.

Patients in a hospital may be connected to a variety of sensors, monitors and devices which produce real-time traces of physiological signals, real-time and near-real-time calculations of physiological parameters. For example, an ICU patient could be simultaneously connected to devices which record ECG, EMG, EEG, capnography, pulse oximetry, pneumography, blood pressure, etc., yielding a plethora of physiological parameters including heart rate, end-tidal $CO_2$ or end-expiratory $CO_2$, $O_2$ saturation, respiratory rate, tidal volume, and minute ventilation. The sheer number of physiological datasets measured from a patient in the hospital can easily lead to information overload.

The information overload can cause healthcare providers to overlook aspects of the data that could indicate important aspects of the patient's condition or the patient's state. Therefore, there is a need to reduce information overload.

SUMMARY OF THE INVENTION

The present invention overcomes the problems and disadvantages associated with current strategies and designs and provides new tools and methods of displaying a physiological dataset in graphical form.

One embodiment of the invention is directed to a method of displaying trends and variability in a physiological dataset. The method comprises the steps of obtaining the physiological dataset, applying a smoothing algorithm to the physiological dataset to obtain a trend of the physiological dataset, applying a variability algorithm to the physiological dataset to obtain the variability of the physiological dataset, outputting a graph of the trend of the physiological dataset, and outputting a graph of the variability of the physiological dataset.

In a preferred embodiment, the physiological dataset is based on data obtained from a patient's respiratory system. Preferably, the smoothing algorithm is one of a moving average algorithm and a digital filter algorithm. The graph of the trend of the physiological dataset and the graph of the variability of the physiological dataset are preferably one of overlaid and graphed adjacently. Preferably, the graph of the variability of the physiological dataset comprises an envelope bounded on the top by a plot of the maximums identified by the variability algorithm and bounded on the bottom by a plot of the minimums identified by the variability algorithm. The space between the bounds is preferably shaded and the graph of the variability of the physiological dataset is preferably used to assess and diagnose apnea.

In a preferred embodiment, the physiological dataset is interbreath interval data. Preferably, the graph of variability of the physiological dataset is a function of fractal scaling coefficients calculated at various time points and over various time windows of the dataset. Preferably, the graph of variability of the physiological dataset comprises one or more of, error bars, line graphs, momentum bars, shaded areas under a curve, and a stochastic plot. In a preferred embodiment, the magnitude of the variability which is displayed by the graph of variability of the physiological dataset is calculated as a function of at least one of, the raw dataset, the smoothed dataset, multiple smoothed datasets, the fractal scaling coefficients of the dataset, or the stochastic coefficients of the dataset.

Another embodiment of the invention is directed toward a device comprising a transthoracic impedance measurement device to obtain a physiological dataset, a processor receiving the physiological dataset from the measurement device, and an output device coupled to the processor. The processor is adapted to: apply a smoothing algorithm to the physiological dataset to obtain a trend of the physiological dataset, apply a variability algorithm to the physiological dataset to obtain the variability of the physiological dataset. The output device is adapted to: output a graph of the trend of the physiological dataset and output a graph of the variability of the physiological dataset.

Another embodiment of the invention is directed toward a system for displaying trends and variability in a physiological dataset. The system comprises a patient monitoring device, at least one sensor coupled to the patient monitoring device, a processor contained within the patient monitoring device and receiving patient data from the at least on sensor, a screen contained within the patient monitoring device and receiving display information from the processor. The processor: obtains the physiological dataset from the at least one sensor, applies a smoothing algorithm to the physiological dataset to obtain a trend of the physiological dataset, applies a variability algorithm to the physiological dataset to obtain the variability of the physiological dataset, outputs a graph of the trend of the physiological dataset to the screen, and outputs a graph of the variability of the physiological dataset to the screen.

In a preferred embodiment, the physiological dataset is based on data obtained from a patient's respiratory system. Preferably, the smoothing algorithm is one of a moving average algorithm and a digital filter algorithm. The graph of the trend of the physiological dataset and the graph of the variability of the physiological dataset are preferably one of overlaid and graphed adjacently. Preferably, the graph of the variability of the physiological dataset comprises an envelope bounded on the top by a plot of the maximums identified by the variability algorithm and bounded on the bottom by a plot of the minimums identified by the variability algorithm. The space between the bounds is preferably shaded and the graph of the variability of the physiological dataset is preferably used to assess and diagnose apnea.

In a preferred embodiment, the physiological dataset is interbreath interval data. Preferably, the graph of variability of the physiological dataset is a function of fractal scaling coefficients calculated at various time points and over various time windows of the dataset. Preferably, the graph of variability of the physiological dataset comprises one or more of, error bars, line graphs, momentum bars, shaded areas under a curve, and a stochastic plot. In a preferred embodiment, the magnitude of the variability which is displayed by the graph of variability of the physiological dataset is calculated as a function of at least one of, the raw dataset, the smoothed dataset, multiple smoothed datasets, the fractal scaling coefficients of the dataset, or the stochastic coefficients of the dataset.

Other embodiments and advantages of the invention are set forth in part in the description, which follows, and in part, may be obvious from this description, or may be learned from the practice of the invention.

DESCRIPTION OF THE DRAWING

The invention is described in greater detail by way of example only and with reference to the attached drawing, in which.

DESCRIPTION OF THE INVENTION

As embodied and broadly described herein, the disclosures herein provide detailed embodiments of the invention. However, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention It has surprisingly been discovered that a visualization of physiological data aids healthcare providers in quickly assessing important features of a monitored physiological parameter by reducing the perceived complexity of a recorded dataset. The invention achieves this by simultaneously displaying a physiological parameter's trend and variability as well as their evolution over time. This is in contrast to existing methods for displaying physiological datasets, which generally include applying various filtering (smoothing) algorithms. Filters generally reduce the perceived complexity of a dataset, enabling a better assessment of trends in the data, but in the process they reduce variability, impairing the ability to assessment changes in variability in the data. Variability has proven to be an important feature of physiological signals. For example, reduced heart rate variability can predict mortality following a heart attack.

A caregiver would not be able to assess heart rate variability from a chart of heart rate where the dataset is filtered. A solution to this problem is to overlay the filtered signal with an indication of variability.

The method described herein is a means of displaying a physiological dataset within a graphical user interface. The dataset is calculated and/or monitored with respect to an independent variable, e.g. time. The dataset is a measurement, calculation or derivation related to a tissue, organ, organ system or physiological system. Features of the time-series analysis including the value, trend of the value and variability of the dataset correlate with specific disease stated related to the monitored tissue, organ or organs system. The features of the time series analysis may also correlate with overall patient health. The method of displaying the dataset enables medical caregivers to quickly assess important time-series features of the dataset.

The method specifically aids in identifying the trend and variability of the dataset with respect to an independent variable, e.g. time. The assessment of variability combined with the trend aids in assessing patient health or diagnosing or predicting disease states.

The dataset may be acquired from the patient by a means of an analog or digital sensor. The dataset may represent a physiological signal or a calculated, estimated or derived physiological parameter or health index. A health index is a numerical representation based on one or more physiological parameters, or features of their signals. The health index correlates with patient health, disease state or overall patient status. In one embodiment of the invention the dataset is a respiratory parameter derived from a transthoracic impedance measurement. In one embodiment the dataset is a calculation of minute ventilation, calculated based on a measurement of transthoracic impedance. In one embodiment the dataset is a respiratory health index based on the combination of variability in tidal volume, the trend in minute ventilation and the duty cycle of the respiratory rate. In another embodiment of the invention, the dataset is the rapid shallow breathing index derived from the patient's respiratory parameters over time.

In one embodiment of the invention, the physiological parameter is Minute Ventilation (MV). The trends in MV combined with an assessment of the variability of MV can assist medical caregivers to identify periods of apnea, hypopnea, hyperventilation, impending respiratory failure/arrest, response to narcotics, pain level, and/or depth of anesthesia.

The method described herein is preferably applied to the dataset first by implementing a filter to reduce the perceived complexity of the dataset. The filter enables the caregiver to quickly assess trends in the data without suffering from information overload of the entire dataset. The filter applied to the dataset may be applied in software or electrical hardware. The filter applied to the dataset may be a time-domain filter or frequency domain filter. The filter may be moving average, a weighted moving average, a smoothing algorithm, a Chebyshev filter, a Butterworth filter, a Bessel filter, an elliptic filter, constant k filter, m-derived filter, special filter, top-hat filter, or other Fourier-transform-based filter. The window of the filter may be 2 minutes, 5 minutes, 10 minutes, 1 hour, a custom time frame, or another time frame and preferably corresponds to the rate at which trends are likely to appear in the data.

Figure 1:
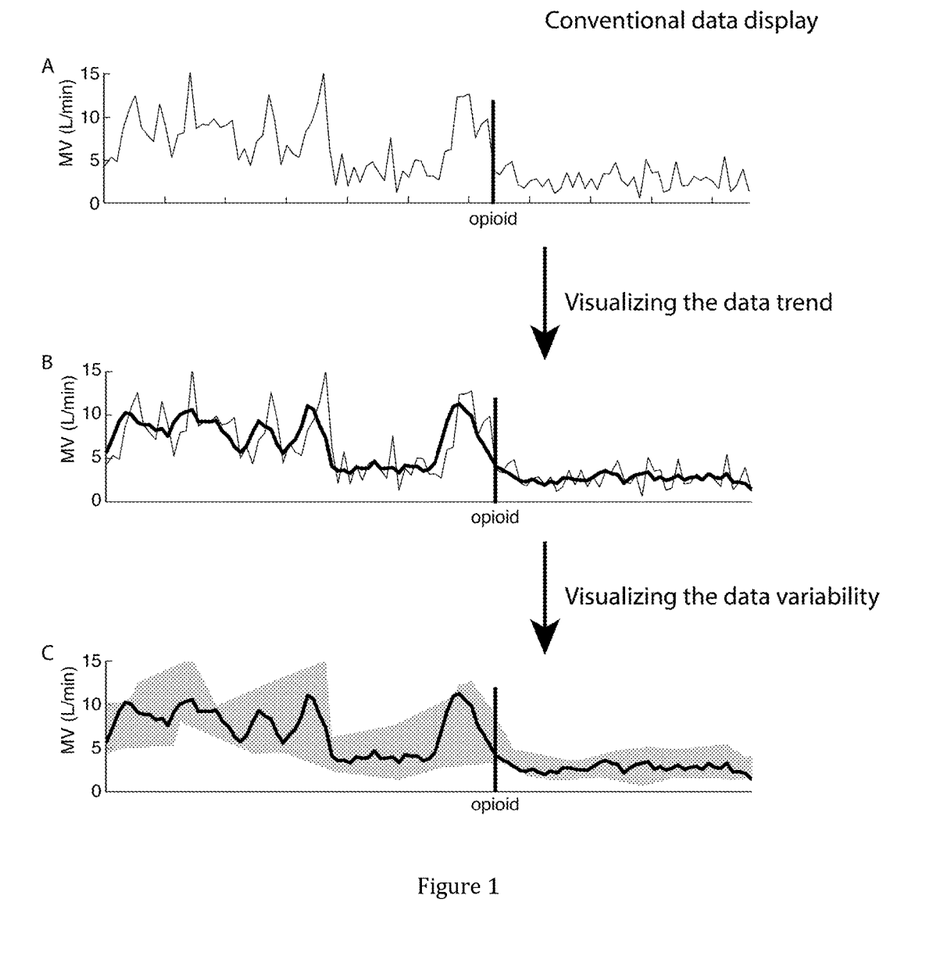
FIG. 1: Example MV trend. (A) Raw data. Note the highly varying signal making it difficult to determine the overall respiratory status. (B) Visualizing a trend in the data. The average trend helps identify general drifts in the measurements. (C) Visualizing the variability in the data. The variability envelope when applied in conjunction with the trend in the data contains all relevant information from the raw signal, yet presents it in an easier-to-comprehend fashion.
Figure 2:
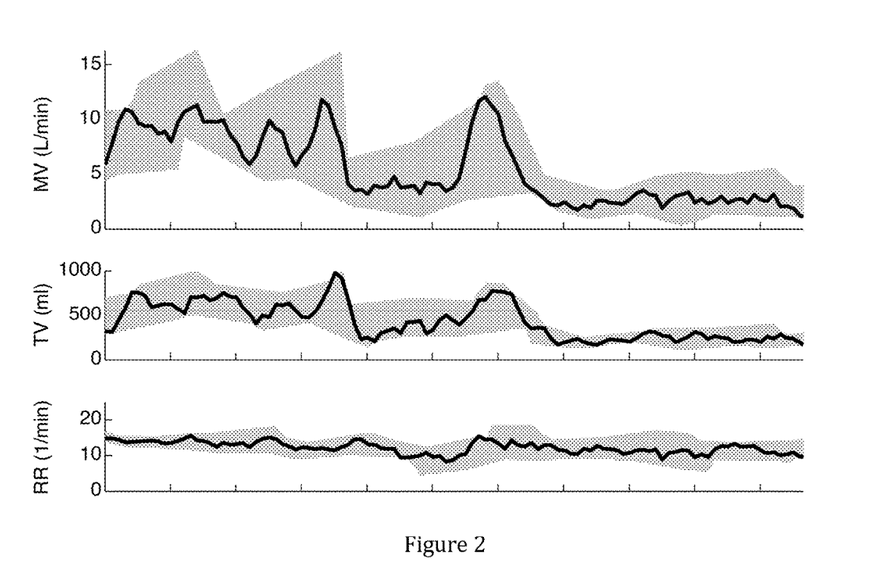
FIG. 2: Examples of average trends and variance envelopes applied to a variety of respiratory signals (MV, TV, RR)

An embodiment of the invention implements a smoothing average over a two-minute window. This smoothed data is then displayed as the trend over time. The middle panel in FIG. 1 shows an example of the smoothed trend line overlaid on the dataset.

After the filter highlights the trend in the data, the method preferably adds a visual indication of variability to the graph. The visual indication of variability preferably consists of an envelope which overlays the smoothed trend. The visualization preferably updates in real-time for monitored parameters, but may be applied retroactively on historical data.

In one embodiment of the invention, the minimum and maximum points within each window are determined and stored in an array of peaks. Preferably once the minimum and maximum points are determined in each window position, all the peaks are plotted on the graph. The maximum peaks are preferably then connected by line segments, with points between the peaks being interpolated. The minimum points are also preferably connected by line segments with points between the minimum peaks being interpolated. The bottom panel in FIG. 1 is an example of this envelope. In this embodiment, the area within the maximum envelope and the minimum envelope may be shaded.

A quantitative coefficient of variability is preferably calculated for each point on the chart and displayed. The coefficient of variability is preferably calculated from a window of data points which is smaller than the total number of points on the graph. The coefficient of variability is preferably based on the statistics of the dataset calculated within the window. The coefficient of variability is preferably a function of statistical variance, standard deviation, or entropy.

In one embodiment, error bars are applied behind the smoothed dataset. The error bars are preferably a function of the standard deviation of the dataset within a window of, for example, 2 minutes. The error bar is preferably overlaid on the graph at the last point in the window, the center point in the window, or the first point in the window.

In one embodiment, a function of one or more fractal scaling coefficients, or a function of a ratio of at least two fractal scaling coefficients is utilized and overlaid on the graph. In one embodiment, a set of fractal scaling coefficients is calculated for the entire dataset (FC1), then again for the window (FC2). The coefficient of variability is preferably calculated as a function of one or more coefficients from the set of FC1 as compared to FC2. One embodiment of the visualization is to display variability as a function of the difference or absolute value of the difference of two or more smoothing algorithms applied to the dataset. In one embodiment of the invention, two moving average algorithms are applied to the dataset, one with a window of ten (10) minutes and one with a window of two (2) minutes. The visualization preferably consists of a graph of the two moving averages overlaid on each other, or both overlaid on the dataset, smoothed or un-smoothed. This may enable the caregiver to see the trend from the smoothed data as well as discern the absolute difference between the smoothed data trends. It is understood that when the two averages cross, i.e. the absolute difference between the two averages reaches zero, the trend in the data has changed direction. This can predict a rapid change in state and trigger an alarm signal.

In another embodiment, the difference between the results of the two smoothing algorithms is calculated and displayed on a graph. The graph is preferably overlaid on the graph of the smoothed dataset, or appears in its own space. This visualization preferably provides an indicator of the momentum behind a trend, where a large difference between the results indicates a strong trend, and a small difference between the results indicates a stable trend. However, a change in sign indicates a reversal of the previous trend.

Another visualization that can be applied to the data is a stochastic plot. The stochastic plot may be overlaid on the raw dataset or a smoothed dataset. The stochastic plot can be interpreted by a care provider to predict a patient's future status.

In one embodiment of the invention, the visualization including a smoothing component and an indication of variability is applied to one or more datasets relating to the respiratory system. The user can interpret the visualization in order to assess or predict patient state, health state, respiratory status, disease state or response to a medical intervention. The user may also use the visualization of variability to diagnose a disease. The user may draw conclusions from the visualization including, an assessment of the patient's response to an opioid, a diagnosis or prediction of respiratory arrest, respiratory failure, apnea or cardiac arrest. The user may assess the patient's respiratory sufficiency, likelihood of successful extubation or the necessity of intubation.

Figure 3:
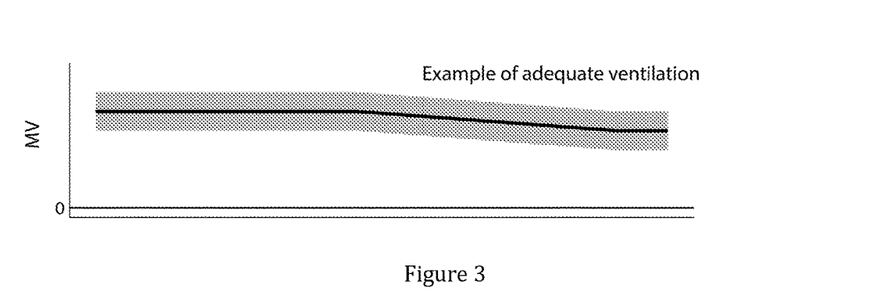
FIG. 3: Example of adequate ventilation (MV) over time, as visualized by a stable trend and a stable envelope.
Figure 11:
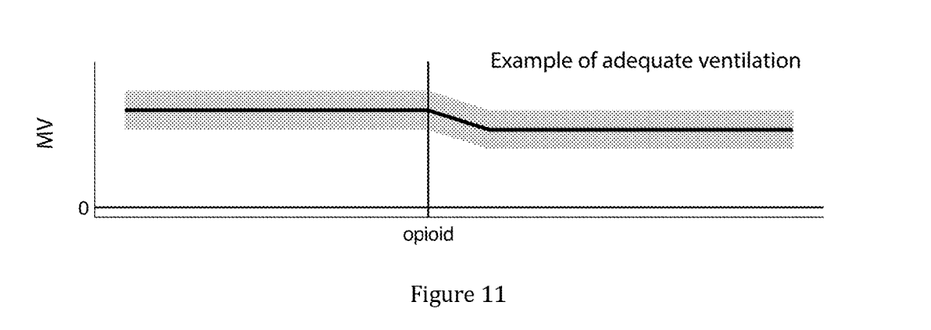
FIG. 11: Example of adequate ventilation (MV) over time, as visualized by a small change in the trend (expected result of opioid administration) and a stable envelope.

FIG. 3 illustrates an example of the display of the visualization algorithm on a minute ventilation dataset. The patient in the example maintains a similar minute ventilation and minute ventilation variability over time. A caregiver could draw the conclusion that the patient has a good status, free of various disease states. FIG. 11 shows an example of a healthy response to an opioid dose, with only a slightly downward trend on the MV dataset, and little change in the signal variability. This type of response would lead a caregiver to conclude that the patient is correctly dosed.

Figure 4:
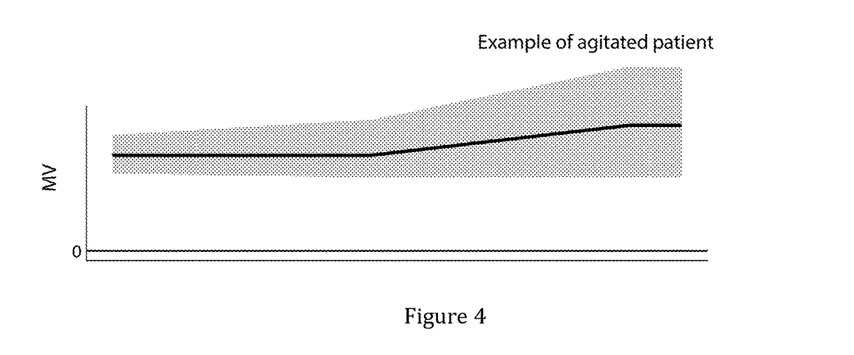
FIG. 4: Example of an agitated patient who may be undermedicated. Note that the trend in the data increases slightly, whereas the envelope increases substantially with time, indicative of increased respiratory variability, likely caused by increase in pain and discomfort.
Figure 9:
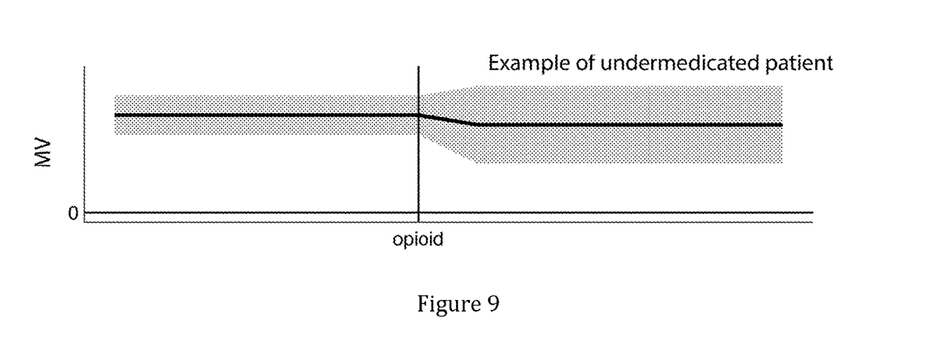
FIG. 9: Example of a patient who may be undermedicated. Note that, despite receiving a dose of opioids, the trend in the data remains practically unchanged, whereas the envelope increases with time, indicative if increased respiratory variability, likely caused by increase in pain and discomfort.

FIG. 4 indicates an example of an agitated patient. In this instance, the increase in MV variability and MV trend as shown in the visualization could lead a caregiver to conclude that the patient is undermedicated and could adjust the patient's dose of pain medication accordingly. FIG. 9 is an example of a patient who responds idiosyncratically to an opioid dose. The variability increases, which could indicate restlessness and discomfort and general inefficacy of the pain medication.

Figure 5:
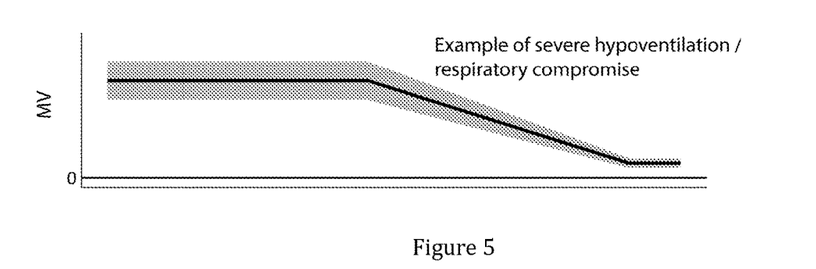
FIG. 5: Example of a patient who is headed towards respiratory compromise. The average MV trend is systematically decreasing and so is the variability in the MV data.
Figure 8:
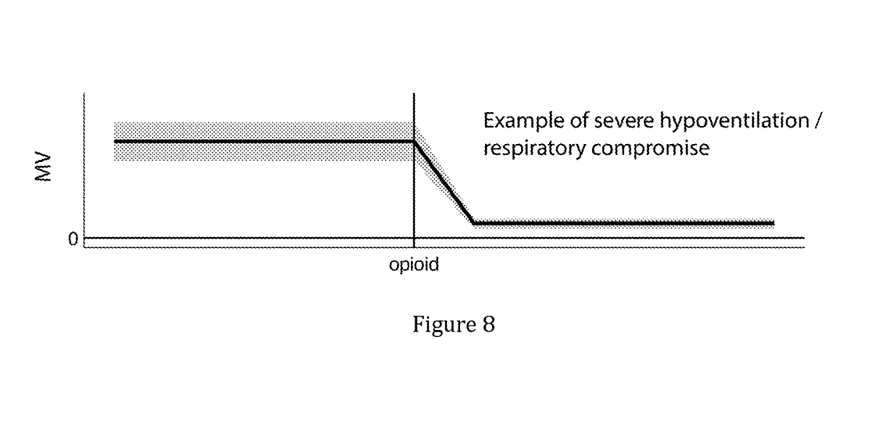
FIG. 8: Example of a patient who is headed towards respiratory compromise following opioid administration. The average MV trend is systematically decreasing and so is the variability in the MV data.

It is often critical for caregivers to respond to indications of respiratory compromise as quickly as possible. The example in FIG. 5 is a case in which a caregiver could use the visualization to diagnose respiratory compromise and undertake a medical intervention to prevent patient state from worsening. Interventions could include waking the patient, administering an opiod antagonist such as Naloxone, or intubating and ventilating the patient. FIG. 8 is an example of the visualization applied to an MV dataset in a patient suffering respiratory compromise as a result of a dose of an opioid.

Figure 6:
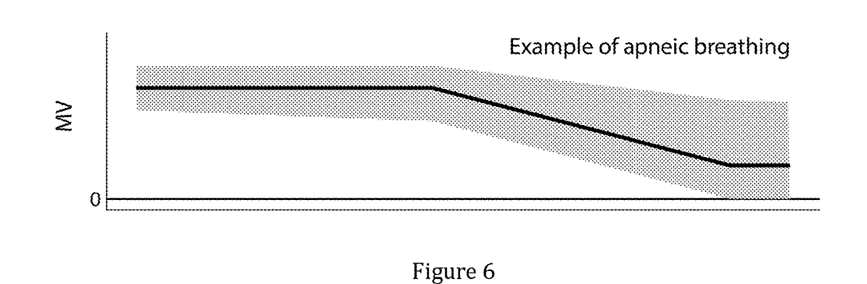
FIG. 6: Example of a patient with apneic breathing pattern. Note the increase in variability (with envelope encroaching on the MV=0 line) coupled with a decrease in the overall trend. This is indicative of a repetitive breathing pattern with significant respiratory pauses and interspersed large "rescue" breaths.
Figure 7:
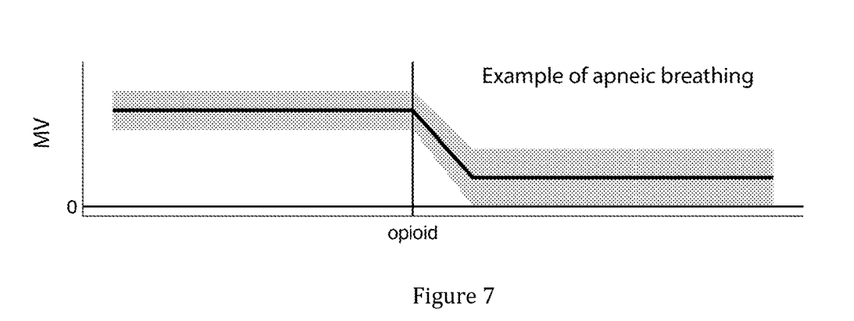
FIG. 7: Example of a patient with apneic breathing pattern as a result of opioid administration. Note the increase in variability (with envelope encroaching on the MV=0 line) coupled with a decrease in the overall trend. This is indicative of a repetitive breathing pattern with significant respiratory pauses and interspersed "rescue" breaths.

Apnea is a state in which the breathing is interrupted. It may result from a variety of causes, including opioid toxicity. The sooner opiate toxicity can be identified, the sooner a caregiver can undertake measures to prevent the patient's condition from worsening. Periods of apnea are generally followed by a period of rescue breathing which may include larger than normal or faster than normal breaths, which normalize over time. The difference between the breaths during these periods translates to a high index of variability in datasets related to the respiratory system. Apnea can be identified by a downward trend in minute volume, a high variability in respiratory rate, or interbreath interval, and a high variability in tidal volume and minute ventilation. FIG. 6 shows an example of the increased variability and decrease in trend in minute ventilation to indicate the onset of apnea. FIG. 7 shows an example of the onset of apnea as a symptom of opioid toxicity in response to a dose of opioid pain medication.

Figure 10:
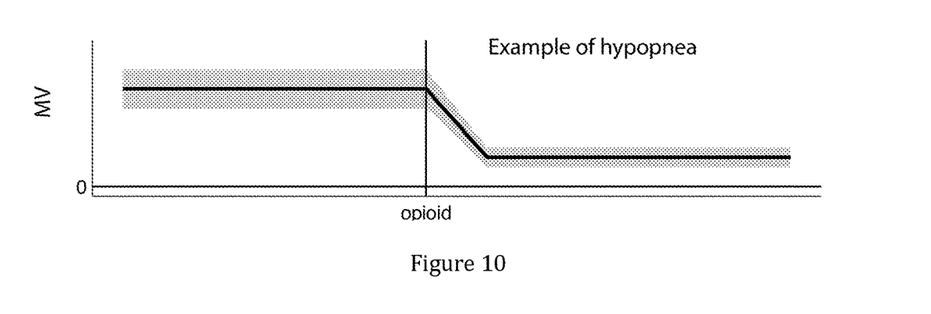
FIG. 10: Example of a patient displaying hypopneic breathing following opioid administration. The decrease in both the trend and variability in the data suggest a regular breathing pattern at lower volumes and rates.

FIG. 10 shows an example of the visualization on the MV dataset in a patient suffering hypopnea, or shallow breathing. In terms of the trend, it is difficult to differentiate hypopnea from apnea, however, the variability in each case is very different. The variability in the hypopneic patient's dataset is much lower, which allows a caregiver to differentiate between the two cases.

The methods disclosed herein may also be applied to parameters associated with the circulatory system including measurements of the heart rate, or its inverse, beat-to-beat interval. Low variability in the heart rate can predict or, indicate, or quantify the progression of many conditions including myocardial infarction, congestive heart failure, diabetic neuropathy, depression or susceptibility to SIDS. In this embodiment, the envelope provides a visualization of heart rate variability to assist the caregiver in identifying, or assessing the risk of the aforementioned conditions.

Figure 13:
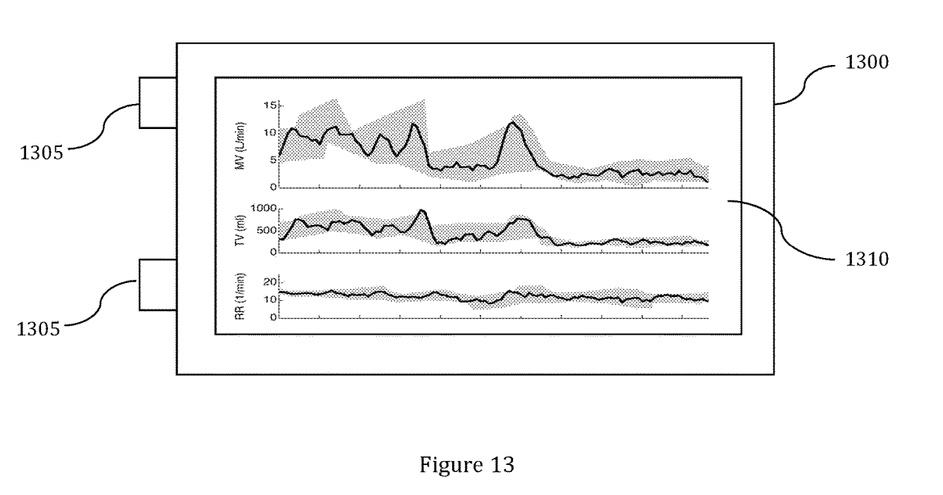
FIG. 13: Example of an embodiment of a patient monitoring device.

FIG. 13 depicts a preferred embodiment of a patient monitoring system 1300 adapted to calculated and display a physiological parameter's trend and variability as well as their evolution over time. Preferably, patient monitoring system 1300 is a portable device that can be mounted on an IV pole, attached to a bed, attached to a wall, placed on a surface or otherwise positioned. Patient monitoring system 1300 may be adapted for use during medical procedures, recovery, and/or for patient monitoring. Preferably, patient monitoring system 1300 is battery powered and/or has a power cable. Patient monitoring system 1300 preferably has at least one input port 1305. Preferably, each input port 1305 is adapted to receive signals from one or more sensors remote to patient monitoring system 1300. Additionally, patient monitoring system 1300 may further include wireless communication technology to receive signals from remote and wireless sensors. The sensors may be adapted to monitor for a specific patient characteristic or multiple characteristics. Patient monitoring system 1300 preferably is adapted to evaluate the data received from the sensors and apply the algorithms described herein to the data. Furthermore, the patient monitoring system 1300 may be able to receive custom algorithms and evaluate the data using the custom algorithm.

Patient monitoring system 1300 preferably further includes a screen or display device 1310. Preferably, screen 1310 is capable of displaying information about patient monitoring system 1300 and the patient being monitored. Screen 1310 preferably displays at least one graph or window of the patient's condition, as described herein. Each graph may be a fixed size or adjustable. For example, the graph may be customizable based on the number of data points, a desired length and/or time of measurement, or a certain number of features (i.e. breaths, breath pauses, or obstructed breaths). Additionally, the scale of the graph may be adjustable. Furthermore, the patient or caregiver (or clinician) may be able to choose what is displayed on screen 1310. For example, screen 1310 may be able to display the mean, median, and/or standard deviation of data being monitored; the max, min and or range of data being monitored; an adaptive algorithm based on trend history; a adapted algorithm based on large populations of like patients (i.e. condition, age, weight, and events); and/or patent breathing parameters (i.e. blood pressure, respiratory rate, $CO_2$, and/or $O_2$ rates).

Patient monitoring system 1300 is preferably equipped with an alarm. The alarm can be an audio alarm and/or a visual alarm. The alarm may trigger based on certain conditions being met. For example, based on trends, real-time conditions, or patient parameter variability. The alarm may be customizable, both in sound/visualization and in purpose. The patient and/or caregiver may be able to navigate through multiple windows that display different information. For example, certain windows may display the graphs described herein, certain windows may display the patient's biographical data, and certain windows may display the system's status. Additionally, custom windows may be added (e.g by the patient, caregiver, or by the system automatically). For example, a custom window may be for clinical use, to mark events, or to display the patient's condition.

In a preferred embodiment, patient monitoring system 1300 has a plurality of configurations. The configurations are preferably adapted to display relevant information to a caregiver or patient about the patient based on the patient's current condition. For example, for a patient undergoing a surgery, the nurse or doctor may need different information than for a patient recovering from an illness. Preferably, at the initiation of monitoring the patient, the patient monitoring system 1300 allows the patient or caregiver to select a configuration. Selectable configurations may include, but are not limited to specific procedures, specific illnesses, specific afflictions, specific patient statuses, specific patient conditions, general procedures, general illnesses, general afflictions, general patient statuses, and/or general patient conditions. Upon selection, preferably, the patient monitoring system 1300 will automatically display data relevant to the selection. In another embodiment, the patient monitoring system 1300 may automatically determine an appropriate configuration based on the data received from the patient. The patient or caregiver may be able to customize configurations once they are chosen.

Figure 12:
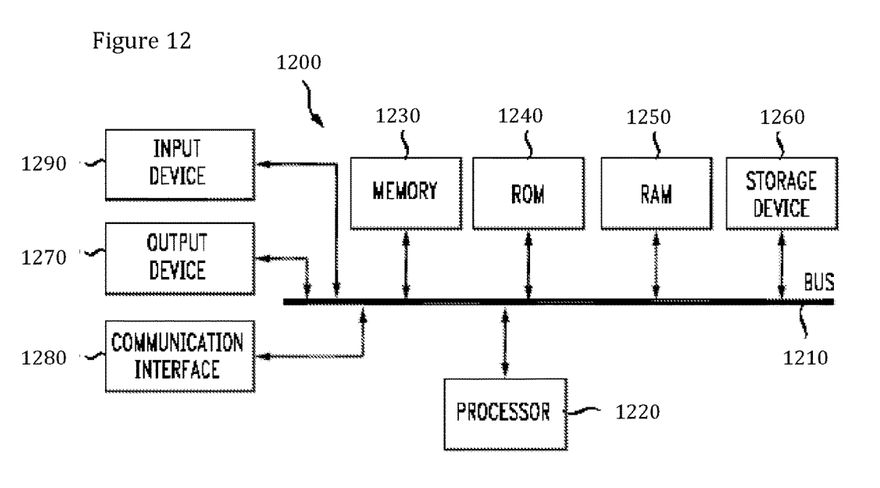
FIG. 12: Example of an embodiment of the structure of the device disclosed herein.

With reference to FIG. 12, an exemplary system includes at least computing device 1200, for example contained within the system depicted in FIG. 13, including a processing unit (CPU) 1220 and a system bus 1210 that couples various system components including the system memory such as read only memory (ROM) 1240 and random access memory (RAM) 1250 to the processing unit 1220. Other system memory 1230 may be available for use as well. It can be appreciated that the invention may operate on a computing device with more than one CPU 1220 or on a group or cluster of computing devices networked together to provide greater processing capability. The system bus 1210 may be any of several types of bus structures including a memory bus or memory controller, a peripheral bus, and a local bus using any of a variety of bus architectures. A basic input/output (BIOS) stored in ROM 1240 or the like, may provide the basic routine that helps to transfer information between elements within the computing device 1200, such as during start-up. The computing device 1200 further includes storage devices such as a hard disk drive 1260, a magnetic disk drive, an optical disk drive, tape drive or the like. The storage device 1260 is connected to the system bus 1210 by a drive interface. The drives and the associated computer readable media provide nonvolatile storage of computer readable instructions, data structures, program modules and other data for the computing device 1200. The basic components are known to those of skill in the art and appropriate variations are contemplated depending on the type of device, such as whether the device is a small, handheld computing device, a desktop computer, a computer server, a handheld scanning device, or a wireless devices, including wireless Personal Digital Assistants ("PDAs"), tablet devices, wireless web-enabled or "smart" phones (e.g., Research in Motion's Blackberry™, an Android™ device, Apple's iPhone™), other wireless phones, a game console (e.g, a Playstation™, an Xbox™, or a Wii™), a Smart TV, a wearable internet connected device, etc. Preferably, the system is technology agnostic.

Although the exemplary environment described herein employs the hard disk, it should be appreciated by those skilled in the art that other types of computer readable media which can store data that are accessible by a computer, such as magnetic cassettes, flash memory cards, digital versatile disks, cartridges, random access memories (RAMs), read only memory (ROM), a cable or wireless signal containing a bit stream and the like, may also be used in the exemplary operating environment.

To enable user interaction with the computing device 1200, an input device 1290 represents any number of input mechanisms, such as a microphone for speech, a touch-sensitive screen for gesture or graphical input, keyboard, mouse, motion input, speech, game console controller, TV remote and so forth. The output device 1270 can be one or more of a number of output mechanisms known to those of skill in the art, for example, printers, monitors, projectors, speakers, and plotters. In some embodiments, the output can be via a network interface, for example uploading to a website, emailing, attached to or placed within other electronic files, and sending an SMS or MMS message. In some instances, multimodal systems enable a user to provide multiple types of input to communicate with the computing device 1200. The communications interface 1280 generally governs and manages the user input and system output. There is no restriction on the invention operating on any particular hardware arrangement and therefore the basic features here may easily be substituted for improved hardware or firmware arrangements as they are developed.

For clarity of explanation, the illustrative system embodiment is presented as comprising individual functional blocks (including functional blocks labeled as a "processor"). The functions these blocks represent may be provided through the use of either shared or dedicated hardware, including, but not limited to, hardware capable of executing software. For example the functions of one or more processors presented in FIG. 12 may be provided by a single shared processor or multiple processors. (Use of the term "processor" should not be construed to refer exclusively to hardware capable of executing software.) Illustrative embodiments may comprise microprocessor and/or digital signal processor (DSP) hardware, read-only memory (ROM) for storing software performing the operations discussed below, and random access memory (RAM) for storing results. Very large scale integration (VLSI) hardware embodiments, as well as custom VLSI circuitry in combination with a general purpose DSP circuit, may also be provided.

Embodiments within the scope of the present invention may also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those of skill in the art will appreciate the preferred embodiments of the invention may be practiced in network computing environments with many types of computer system configurations, including personal computers, hand-held devices, multi-processor systems, microprocessor-based or programmable consumer electronics, network PCs, minicomputers, mainframe computers, and the like. Networks may include the Internet, one or more Local Area Networks ("LANs"), one or more Metropolitan Area Networks ("MANs"), one or more Wide Area Networks ("WANs"), one or more Intranets, etc. Embodiments may also be practiced in distributed computing environments where tasks are performed by local and remote processing devices that are linked (either by hardwired links, wireless links, or by a combination thereof) through a communications network, e.g. in the "cloud." In a distributed computing environment, program modules may be located in both local and remote memory storage devices.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

The invention claimed is:

1. A method of displaying trends and variability in a physiological dataset, comprising, on a processor:
   obtaining the physiological dataset;
   applying a smoothing algorithm to the physiological dataset to obtain a trend of the physiological dataset;
   applying a variability algorithm to the physiological dataset to obtain the variability of the physiological dataset;
   outputting a real-time graph of the trend of the physiological dataset;
   outputting a real-time graph of the variability of the physiological dataset overlaid on the graph of the trend of the physiological dataset, wherein the graph of the variability of the physiological dataset comprises a real time visual envelope bounded on the top by a plot of the maximums identified by the variability algorithm and bounded on the bottom by a plot of the minimums identified by the variability algorithm, where said maximums and minimums are identified within each time window over which the variability is estimated; and
   triggering at least one of an audible or visual alarm upon a predetermined condition in the variability or trend of the physiological dataset being met whereas the predetermined condition is based on at least one of: (1) ratio between variability and trend values within a time window, (2) difference between maximum and minimum within a time window, (3) the value of the trend within a time window, (4) the change in the trend values from one window to the next, (5) the change in the difference between maximum and minimum within a time window from one window to the next, or (6) area within the maximum envelope and the minimum envelope.

2. The method of claim 1, wherein the physiological dataset is based on data obtained from a patient's respiratory system.

3. The method of claim 1, wherein the smoothing algorithm is one of a moving average algorithm and a digital filter algorithm.

4. The method of claim 1, wherein the space between the bounds is shaded.

5. The method of claim 4, wherein the graph of the variability of the physiological dataset is used to assess and diagnose apnea.

6. The method of claim 1, wherein the physiological dataset is interbreath interval data.

7. The method of claim 1, wherein the graph of variability of the physiological dataset is a function of fractal scaling coefficients calculated at various time points and over various time windows of the dataset.

8. The method of claim 1, wherein the graph of variability of the physiological dataset comprises one or more of, error bars, line graphs, momentum bars, shaded areas under a curve, and a stochastic plot.

9. The method of claim 1, wherein the magnitude of the variability which is displayed by the graph of variability of the physiological dataset is calculated as a function of at least one of, the raw dataset, the smoothed dataset, multiple smoothed datasets, the fractal scaling coefficients of the dataset, or the stochastic coefficients of the dataset.

10. A device comprising:
    a transthoracic impedance measurement device to obtain a physiological dataset;
    a processor receiving the physiological dataset from the measurement device, to:
    apply a smoothing algorithm to the physiological dataset to obtain a trend of the physiological dataset; and
    apply a variability algorithm to the physiological dataset to obtain the variability of the physiological dataset;
    an output device coupled to the processor to:
    output a real-time graph of the trend of the physiological dataset; and
    output a real-time graph of the variability of the physiological dataset overlaid on the graph of the trend of the physiological dataset, wherein the graph of the variability of the physiological dataset comprises a real time visual envelope bounded on the top by a plot of the maximums identified by the variability algorithm and bounded on the bottom by a plot of the minimums identified by the variability algorithm, where said maximums and minimums are identified within each time window over which the variability is estimated; and
    at least one of an audible or visual alarm, wherein the alarm is triggered upon a predetermined condition in the variability or trend of the physiological dataset being met, wherein the predetermined condition is based on at least one of: (1) ratio between variability and trend values within n a time window, (2) difference between maximum and minimum within a time window, (3) the value of the trend within a time window, (4) the change in the trend values from one window to the next, (5) the change in the difference between maximum and minimum within a time window from one window to the next, or (6) area within the maximum envelope and the minimum envelope.

11. A system for displaying trends and variability in a physiological dataset, comprising:
    a patient monitoring device;

at least one sensor coupled to the patient monitoring device;

a processor contained within the patient monitoring device and receiving patient data from the at least on sensor;

a screen contained within the patient monitoring device and receiving display information from the processor; and at least one of an audible or visual alarm1, wherein the alarm is triggered upon a predetermined condition in the variability or trend of the physiological dataset being met, wherein the predetermined condition is based on at least one of: (1) ratio between variability and trend values within a time window, (2) difference between maximum and minimum within a time window, (3) the value of the trend within a time window, (4) the change in the trend values from one window to the next, (5) the change in the difference between maximum and minimum within a time window from one window to the next, or (6) area within the maximum envelope and the minimum envelope;

wherein the processor:

obtains the physiological dataset from the at least one sensor;

applies a smoothing algorithm to the physiological dataset to obtain a trend of the physiological dataset;

applies a variability algorithm to the physiological dataset to obtain the variability of the physiological dataset;

outputs a real-time graph of the trend of the physiological dataset to the screen; and outputs a real-time graph of the variability of the physiological dataset to the screen overlaid on the graph of the trend of the physiological dataset, wherein the graph of the variability of the physiological dataset comprises a real time visual envelope bounded on the top by a plot of the maximums identified by the variability algorithm and bounded on the bottom by a plot of the minimums identified by the variability algorithm, where said maximums and minimums are identified within each time window over which the variability is estimated.

12. The system of claim 11, wherein the physiological dataset is based on data obtained from a patient's respiratory system.

13. The system of claim 11, wherein the smoothing algorithm is one of a moving average algorithm and a digital filter algorithm.

14. The system of claim 11, wherein the space between the bounds is shaded.

15. The system of claim 14, wherein the graph of the variability of the physiological dataset is used to assess and diagnose apnea.

16. The system of claim 11, wherein the physiological dataset is interbreath interval data.

17. The system of claim 11, wherein the graph of variability of the physiological dataset is a function of fractal scaling coefficients calculated at various time points and over various time windows of the dataset.

18. The system of claim 11, wherein the graph of variability of the physiological dataset comprises one or more of, error bars, line graphs, momentum bars, shaded areas under a curve, and a stochastic plot.

19. The system of claim 11, wherein the magnitude of the variability which is displayed by the graph of variability of the physiological dataset is calculated as a function of at least one of, the raw dataset, the smoothed dataset, multiple smoothed datasets, the fractal scaling coefficients of the dataset, or the stochastic coefficients of the dataset.

20. The method of claim 1, further comprising the step of attaching the processor to an IV pole.

21. The device of claim 10, wherein the device is adapted to be coupled to an IV pole.

22. The system of claim 11, wherein the patient monitoring device is adapted to be coupled to an IV pole.

* * * * *